United States Patent
Demas et al.

(10) Patent No.: US 10,568,636 B2
(45) Date of Patent: Feb. 25, 2020

(54) COMPRESSION DEVICE

(71) Applicant: Swift-Strap LLC, Watertown, MA (US)

(72) Inventors: Nickolas Peter Demas, Cambridge, MA (US); Anton Stuart Hunt, Houston, TX (US)

(73) Assignee: Swift-Strap LLC, Watertown, MA (US)

( * ) Notice: Subject to any disclaimer, the term of this patent is extended or adjusted under 35 U.S.C. 154(b) by 112 days.

(21) Appl. No.: 15/556,115

(22) PCT Filed: Mar. 17, 2016

(86) PCT No.: PCT/US2016/022882
§ 371 (c)(1),
(2) Date: Sep. 6, 2017

(87) PCT Pub. No.: WO2016/149502
PCT Pub. Date: Sep. 22, 2016

(65) Prior Publication Data
US 2018/0042616 A1    Feb. 15, 2018

Related U.S. Application Data

(60) Provisional application No. 62/135,679, filed on Mar. 19, 2015, provisional application No. 62/201,454, filed on Aug. 5, 2015.

(51) Int. Cl.
*A61B 17/132* (2006.01)
*F16B 2/08* (2006.01)
(Continued)

(52) U.S. Cl.
CPC ...... *A61B 17/1327* (2013.01); *A61B 17/1322* (2013.01); *F16B 2/08* (2013.01); *F16B 2/185* (2013.01); *B65D 63/16* (2013.01)

(58) Field of Classification Search
CPC ............. A61B 17/1322; A61B 17/132; A61B 17/1327; F16B 2/08
See application file for complete search history.

(56) References Cited

U.S. PATENT DOCUMENTS 1,447,967 A   3/1923   Davis
2,113,534 A   4/1938   Brown
(Continued)

FOREIGN PATENT DOCUMENTS

WO    WO 2015/119968    8/2015

OTHER PUBLICATIONS

Extended European Search Report for EP Application No. 16765747.7, entitled "Compression Device," Dated: Dec. 10, 2018 (9 pgs).
(Continued)

*Primary Examiner* — Shaun L David
*Assistant Examiner* — Christina C Lauer
(74) *Attorney, Agent, or Firm* — Hamilton, Brook, Smith and Reynolds, P.C.

(57) ABSTRACT

A compression device, useful for applying circumferential compression to an object, includes a simplified cinch mechanism. The device includes a guidance slide, a jamming feature/pull tab, a buckle assembly and a cinch strap, which form a loop for placing about an object. The cinch strap includes both an inner portion, anchored to the jamming feature, and an outer portion, anchored to the guidance slide. The inner portion of the cinch strap passes through the guidance slide to an adjustable, locking side of the buckle assembly, and the outer portion of the cinch strap passes from the adjustable, locking side of the buckle assembly to the guidance slide. The cinch strap can move freely when pulled on by the inner portion and lock when pulled on by the outer portion, such that an inner circumference of the (Continued)

device is adjustable but can maintain a minimum circumferential length after tension is applied.

12 Claims, 3 Drawing Sheets

(51) Int. Cl.
*F16B 2/18* (2006.01)
*B65D 63/16* (2006.01)

(56) References Cited

U.S. PATENT DOCUMENTS

| | | | | |
|---|---|---|---|---|
| 2,152,922 | A | * | 4/1939 | Robinson .......... A61F 13/00034 606/203 |
| 2,754,825 | A | | 7/1956 | Richmond |
| 6,217,601 | B1 | * | 4/2001 | Chao .................. A61B 17/1325 606/203 |
| 6,899,720 | B1 | | 5/2005 | McMillan |
| 6,960,223 | B1 | | 11/2005 | Ambach |
| 7,776,064 | B2 | | 8/2010 | Jennifer et al. |
| 7,892,253 | B2 | | 2/2011 | Esposito et al. |
| 8,343,182 | B2 | | 1/2013 | Kirkham |
| 8,561,268 | B2 | | 10/2013 | Hortnagl |
| 8,652,164 | B1 | | 2/2014 | Aston |
| 2005/0049630 | A1 | * | 3/2005 | Ambach .......... A61B 17/1327 606/203 |
| 2005/0240217 | A1 | | 10/2005 | Johnson et al. |
| 2009/0062842 | A1 | | 3/2009 | Esposito et al. |
| 2010/0049241 | A1 | | 2/2010 | Persson |
| 2010/0057120 | A1 | * | 3/2010 | Kirkham ............ A61B 17/1322 606/203 |
| 2012/0071917 | A1 | | 3/2012 | McDonald et al. |
| 2015/0051638 | A1 | | 2/2015 | Dickinson et al. |
| 2016/0345981 | A1 | | 12/2016 | Demas et al. |

OTHER PUBLICATIONS

Notice of Allowance for U.S. Appl. No. 15/116,488, entitled "Compression Device," Dated: Jan. 10, 2019 (7 pgs).
Corrected Notice of Allowability for U.S. Appl. No. 15/116,488, entitled "Compression Device," Dated: Mar. 19, 2019 (6 pgs).
Office Action from U.S. Appl. No. 15/116,488, "Compression Device," dated Sep. 10, 2018.
Notification Concerning Transmittal of International Preliminary Report on Patentability, "Compression Device," PCT/US2015/014306, dated Aug. 18, 2016.
Notification of Transmittal of the International Search Report and the Written Opinion of the International Searching Authority, or the Declaration., "Compression Device", PCT/US2016/022882, dated Jul. 13, 2016.
Notification of Transmittal of the International Search Report and the Written Opinion of the International Searching Authority, or the Declaration, "Compression Device," PCT/US2015/014306, dated Apr. 23, 2015.

* cited by examiner

COMPRESSION DEVICE

RELATED APPLICATIONS

This application is the U.S. National Stage of International Application No. PCT/US2016/022882, filed Mar. 17, 2016, which designates the U.S., published in English, and claims the benefit of U.S. Provisional Application No. 62/201,454, filed on Aug. 5, 2015 and U.S. Provisional Application No. 62/135,679, filed Mar. 19, 2015. The entire teachings of the above applications are incorporated herein by reference.

BACKGROUND

There are several tourniquets on the market that can be used in cases of severe limb hemorrhage. Such tourniquets typically involve cinching, to remove slack from the tourniquet, followed by tightening, to apply pressure to the limb. Many tourniquets have been made as devices that require two hands to effectively apply them, making them inappropriate for self-application. A few tourniquets that are applicable with just one hand, of the type described in U.S. Pat. Nos. 7,892,253 and 7,776,064, require dexterity to cinch using cumbersome one-way buckle and/or clasp features, which cost valuable time when self-applying the device in a high stress scenario. This proves to be a hindrance in the cinching process, making the application of the tourniquet difficult and slow.

U.S. Pat. No. 6,960,223 describes a tourniquet that may be applied with one hand with gross motor skills, or minimal dexterity. This tourniquet consists of two concentric loops formed such that pulling on the outer cinches the inner loop. However, pulling on the outer loop also creates friction between the loops, preventing the mechanism from effectively working. This locking friction effect makes it more troublesome for the user to apply the device, if at all. This complication again leads to longer application times, especially in high stress scenarios. In the case of a tourniquet, a longer application time can be critical to the survival chances of the user.

Many tourniquets have been made as devices that can be applied only on limbs with an accessible open end. These tourniquets are in the form of closed loops and can only be slid on from an open end, making them impossible to apply on entrapped or severely mangled limbs. A few tourniquets that are applicable on such limbs, of the type described in U.S. Pat. No. 8,343,182, are in the form of open loops that may be closed during application. However, accidental opening of the loop after application is a concern with these tourniquets. Additionally, significant dexterity is required to open and close the overall device loop.

U.S. Pat. No. 8,652,164 describes a ratcheting tourniquet which can be tightened using gross motor skills or minimal dexterity. However, the cinch method is cumbersome: the loosely-bound device has to be anchored using either the teeth or another limb, if available, to fully affect the cinch prior to the ratchet tightening. This adds an extra step, and slows down the overall application of the device.

SUMMARY OF THE INVENTION

Described is a simple, mechanical device for applying compression on an object. One particular application is as a medical device, specifically, as a tourniquet. As a tourniquet, the device can be clamped down firmly around a limb proximal to an injury and, further, can be secured very tightly to occlude blood vessels in the limb and stop blood flow. The device can be used in cases of hemorrhage to avoid unconsciousness and even death due to excessive blood loss. It is designed for a range of applications where excessive extremity hemorrhage may occur, for example, for use by soldiers in active war zones or for use by first-responders (e.g., police, emergency medical services) in the case of civilian medical emergencies. Compression devices can be beneficial in other applications where circumferential pressure is required (e.g., bundling and hauling, hoisting), as well as for securing or anchoring to objects (e.g., safety harness anchor at height, tarpaulin anchor, hammock hanger), among others.

Compression devices and methods are disclosed in International Application Number PCT/US15/14306, published as WO2015/119968, the entire teachings of which are incorporated herein by reference. Embodiments of the present invention are improvements to the devices of International Application Number PCT/US15/14306 and use half of a cinch mechanism, reducing the complexity of the device while improving the effectiveness of the cinch procedure. The device of the present invention can be applied quickly in two steps. First, the user pulls on the cinch strap to rapidly tighten the device snugly onto a limb and remove slack from the device. Second, the user affects a mechanical advantage tightening mechanism, such as a ratcheting buckle, windlass, or other tightening mechanism, increasing circumferential force in the device and causing additional pressure to be applied to the limb. This pressure can be large enough to occlude all or most blood vessels within the hemorrhaging limb. With application of the device proximal to an injury, bleeding ceases once the device is tight.

Compression devices of the present invention include a rapid-cinch paradigm that allows for a user to quickly and effectively snug the device against a limb before actuating a mechanical advantage tightening mechanism. A difference between embodiments of this invention and the devices described in International Application Number PCT/US15/14306 is that the rapid cinch paradigm of the present invention is effected through a single primary cinch loop, rather than two primary cinch loops as described in the PCT/US15/14306 application.

The rapid cinch mechanism includes an inner loop primary pull, ensuring that the outer loop does not trap and lock up the inner loop (e.g., by friction) when affecting the cinch, as, for example, occurs with the device disclosed in U.S. Pat. No. 6,960,223. In addition, the rapid cinch mechanism can include a simple buckle, which allows the user to open and close the device loop without requiring cumbersome and dexterous maneuvers to slide a strap out of, and back into, a buckle arrangement, as is required by the devices disclosed in U.S. Pat. Nos. 7,892,253, 7,776,064, 8,343,182 and 8,652,164. Advantageously, the rapid-cinch mechanism of the present approach can be operated with only gross motor skill and one simple step to cinch: pulling on a pull-tab to cinch without the need for any anchoring. In contrast, anchoring is required, for example, by the device disclosed in U.S. Pat. No. 8,652,164.

An example of a compression device includes a guidance slide, a jamming feature, which can also be a pull tab, a buckle assembly and a cinch strap. The buckle assembly includes both an adjustable, locking side and a non-adjustable side. The cinch strap includes both an inner portion and an outer portion, the inner portion anchored to the jamming feature, and the outer portion anchored to the guidance slide. The cinch strap passes through the adjustable, locking side of the buckle assembly in such a way that pulling on the outer portion locks the adjustable, locking side and pulling on the inner portion allows the cinch strap to move freely through the adjustable, locking side. The inner portion of the cinch strap passes through the guidance slide to the adjustable, locking side of the buckle assembly, and the outer portion of the cinch strap passes from the adjustable, locking side of the buckle assembly to the guidance slide. The non-adjustable side of the buckle assembly is coupled to the guidance slide and the buckle assembly releasably mates the adjustable, locking side and non-adjustable side. The coupled buckle assembly and cinch strap inner portion form a loop for placing about an object. The inner circumference of the cinch strap is adjustable by pulling the jamming feature, which is connected to the inner portion of the cinch strap. The outer circumference of the cinch strap is configured to maintain a minimum circumferential length after tension on the jamming feature is applied.

A compression device can further include a tightening mechanism connecting the non-adjustable side of the buckle assembly to the guidance slide. The tightening mechanism can be a self-holding ratcheting buckle system. The jamming feature can also be a pull-tab, such as, for example, a D-ring. The adjustable, locking side and non-adjustable side of the buckle assembly can be separable from each other. The buckle assembly can include a male stabbing buckle with an adjustable, locking side and female buckle with a non-adjustable side. The adjustable, locking side of the buckle assembly can include an adjustable bar or a stationary bar, the stationary bar enabling a locking action by friction between the inner and outer cinch straps. The cinch strap can be webbing.

Another example of a compression device includes a guidance slide, a single-direction locking mechanism, and a cinch strap with both an inner portion and an outer portion. The outer portion is anchored to the guidance slide. The cinch strap passes through the single-direction locking mechanism in such a way that pulling on the outer portion causes the locking mechanism to lock the cinch strap and pulling on the inner portion allows the cinch strap to move freely through the locking mechanism. The inner portion of the cinch strap passes from the locking mechanism through the guidance slide. The locking mechanism is coupled to the guidance slide. The inner portion of the cinch strap and the coupled locking mechanism and guidance slide form a loop for placing about an object, with the inner circumference of the cinch strap being adjustable by pulling the inner portion of the cinch strap, and the outer circumference of the cinch strap configured to maintain a minimum circumferential length after tension on the inner portion is applied.

A method of compressing an object includes providing a compression device, placing the loop of the device about the object, and tightening the loop around the object by pulling the inner portion of the cinch strap.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
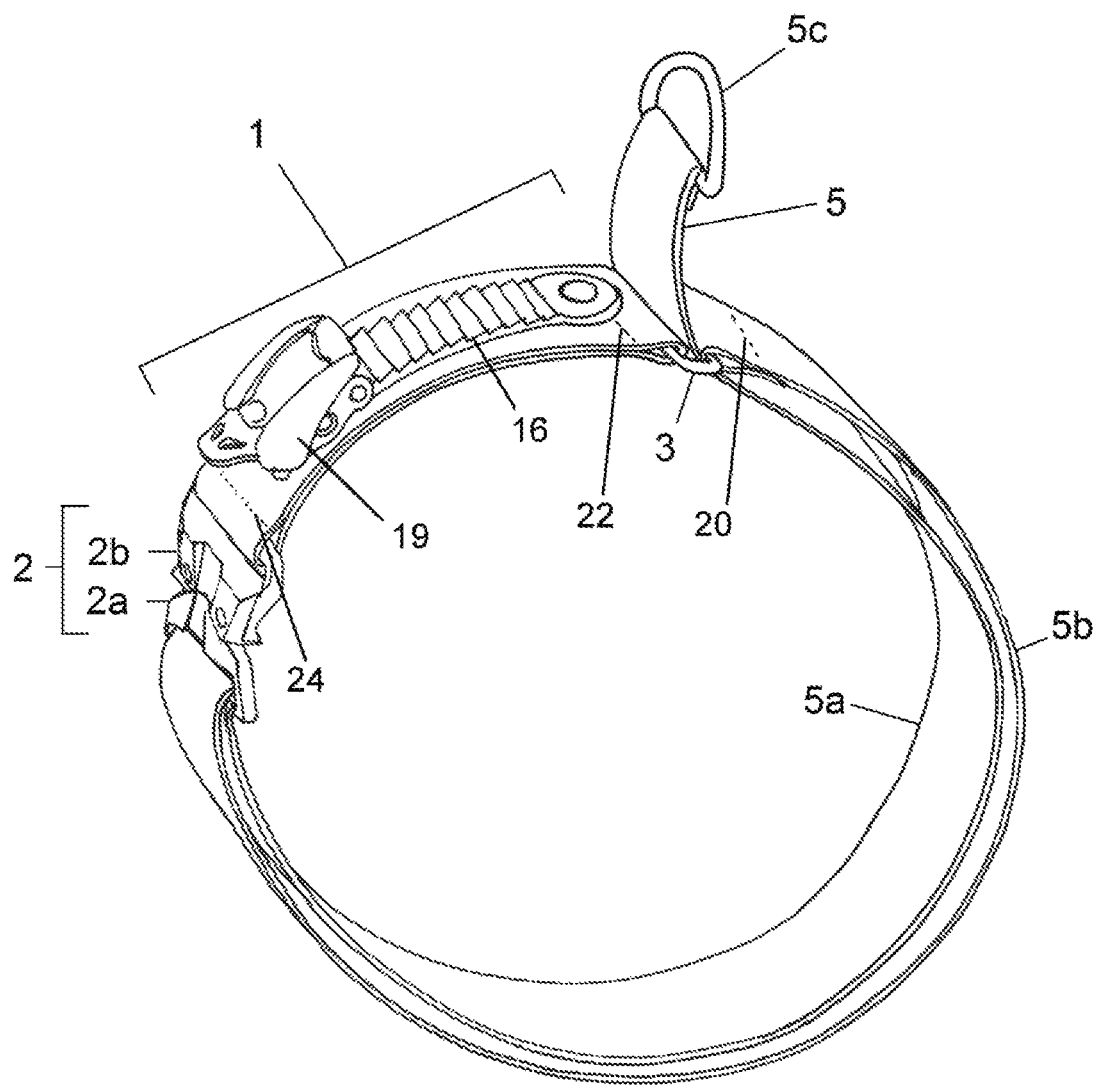
FIG. 1 illustrates an example of a compression device.

FIG. 1 shows an overview of an example of a compression device. A tightening mechanism [1] is fixed to a non-adjustable side [2b] of a buckle assembly [2], which consists of an adjustable side [2a] and a non-adjustable side [2b]. The other side of the tightening mechanism [1] is fixed to a guidance slide [3]. The tightening mechanism can be a ratcheting buckle mechanism, as shown in FIG. 1, or a windlass or other device to affect a mechanical advantage and apply a circumferential force, such as those described in International Application Number PCT/US15/14306. The cinch strap [5] includes a jamming feature/pull-tab [5c] at one end. In FIG. 1, a D-ring functions as the jamming feature/pull-tab. The D-ring cannot pass through the guidance slide [3], keeping the device from coming apart, while also providing a location at which a user may easily grab the cinch strap using only gross motor skills, for example, as may be necessitated if the device is blood- or water-soaked, if the user has gloved hands, or the like. The jamming feature can include, either in addition to a D-ring or in place of a D-ring, an oversized rivet, multi-layer fabric bundle, or other mechanical element that keeps the loose end of the cinch strap [5] from being pulled through the guidance slide [3]. As mentioned, the D-ring illustrated in FIG. 1 also functions as a pull-tab, but this pull-tab need not be one in the same with the jamming feature. For example, a loop of strap could function as the pull-tab and a rivet to fix a loop back against the strap could function as the jamming feature. Other configurations of the jamming feature and pull-tab are possible.

Figure 2:
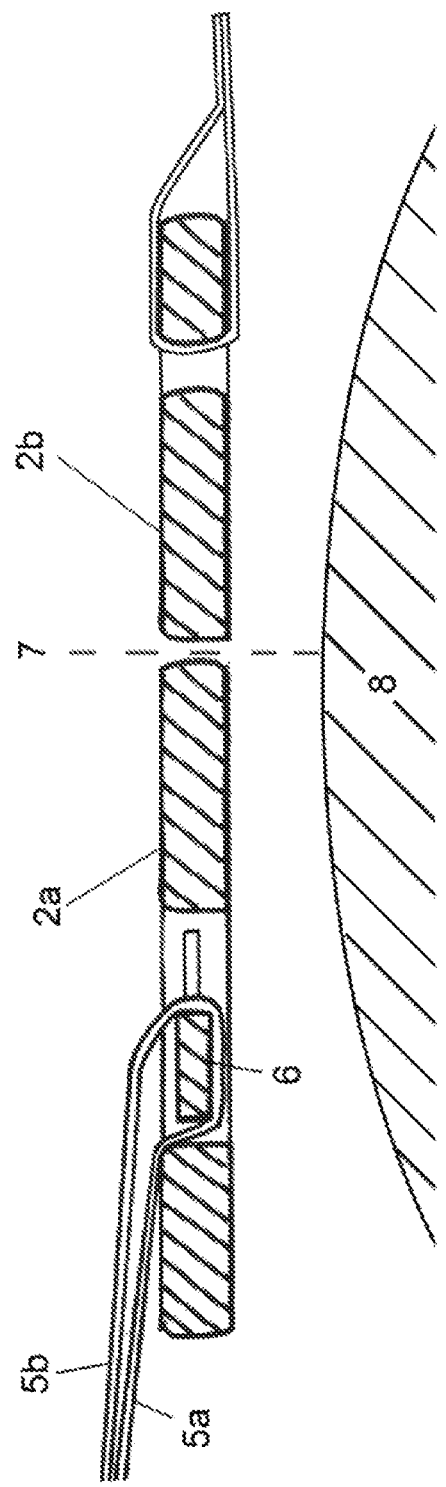
FIG. 2 is a cross-sectional view of a buckle assembly.

From the jamming feature, the cinch strap [5] then passes through the guidance slide [3]. From the guidance slide [3], the inner portion of the cinch strap [5a] extends to the adjustable side [2a] of the buckle assembly [2] and is routed as shown in FIG. 2 around an adjustable bar [6] with respect to the limb [8]. The cinch strap emerges from the adjustable side [2a] of the buckle assembly [2] and passes back on the outside of the device to the guidance slide [3], to which it is fixed, forming an outer portion of the cinch strap [5b].

To perform the cinch step, the jamming feature/pull-tab [5c] is pulled away from the limb. This removes slack in the device, bringing the device snug against the limb. The tightening mechanism [1] can then be actuated effectively. Again, the D-ring illustrated in FIG. 1 acts as both the jamming feature/pull-tab [5c] that prohibits the loose end of the cinch strap [5] from falling through the guidance slide [3], which would cause the device to unravel.

The strap routing can providefor a rapid cinch application of the device. By pulling on the jamming feature/pull-tab [5c] the inner portion of the cinch strap [5a] is first easily cinched down to the required object/limb circumference with minimal resistance. The frictional resistance in the adjustable side [2a] of the buckle assembly [2] can ensure that this step happens to completion first. Once the inner portion of the cinch strap [5a] has been cinched to the object/limb size, the outer portion of the cinch strap [5b] is then free to cinch down to the same object/limb size. A small frictional resistance in the adjustable side [2a] of the buckle assembly [2] can be overcome to complete the cinch, along with minimal sliding friction against the limb. Tension is held in the cinched device loop between the rigid attachment of the outer portion [5a] of the cinch strap to guidance slide

[3] and the adjustable side [2a] of the buckle assembly [2] which locks when tension is applied to [5b].

The inner-to-outer ([5a] to [5b]) cinch paradigm, unlike the outer-to-inner cinch paradigm shown, for example, in U.S. Pat. No. 6,960,223, ensures that the straps (e.g., inner cinch strap [5a] and outer cinch strap [5b]) do not compress against each other during cinching, which can lead to excessive frictional resistances and can stop the device from cinching down effectively under normal use. An inner-to-outer cinch paradigm is described in International Application Number PCT/US15/14306. Advantageously, embodiments of this invention use a single complete inner-to-outer loop, whereas the aforementioned PCT application discloses a two-loop design.

The assembly of the cinch strap [5] and elements of the tightening mechanism [1] include webbing or strap material. The webbing or strap material can be in the form of flexible elongated members, allowing for easy passage of the webbing or strap material through guidance slide [3], as well as allowing for effective passage through the adjustable side [2a] of the buckle assembly [2]. The width of the webbing or strap material can be variable, and can be adjusted depending on application of the compression device. Specifically, wider webbing or strap materials can be used for a lower pressure distribution profile (e.g., compressive force is spread over a larger area) whilst less wide webbing or strap material can be used for a higher pressure distribution profile (e.g., compressive force is spread across a smaller area). To complete the assembly of the device in FIG. 1 using the webbing or strap material, anchor points can be included. As illustrated in FIG. 1, three anchor points are included to assemble the device. Additional anchor points can be included in the assembly of tightening mechanism [1]. As shown through dashed lines in FIG. 1, a first anchor point [20] attaches the outer potion of the cinch strap [5b] to one side of guidance slide [3]. A second anchor point [22] attaches one side of tightening mechanism [1] to the other side of guidance slide [3]. A third anchor point [24] attaches the other side of tightening mechanism [1] to the non-adjustable side [2b] of the buckle assembly [2]. The anchor points [20, 22, 24] can be formed by, for example but not restricted to, sewing, gluing, stapling, clamping, heat/ultrasound (sonic) welding, or any combinations thereof With respect to FIG. 2, when tension is applied on the inner portion of the cinch strap [5a], the adjustable bar [6] opens and allows for the outer portion of the cinch strap [5b] to pass through the adjustable side [2a] and to become the inner portion of the cinch strap [5a],reducing the overall circumference of the device. This can occur when the cinch strap [5] is pulled by the jamming feature/pull-tab [5c] and a rapid, smooth cinch can be accomplished. When tension is applied on the outer portion of the cinch strap [5b], the adjustable bar [6] closes against the cinch strap [5] and prohibits the cinch strap [5] from moving. This can occur when tension on the jamming feature/pull-tab [5c] is released and the device maintains, in the presence of circumferential tension, the minimum circumferential length attained when tension on jamming feature/pull-tab [5c] was applied.

The routing of the cinch strap can be modified from the design shown in FIG. 2 to remove the adjustable bar [6], as it has been noted that friction between the straps when cinched may be adequate in some applications to hold the device tight at the minimum circumferential length.

The buckle assembly [2] can be separable, opening at the separation point [7] to allow for the easy application of the compression device to a trapped or mangled limb. Such a scenario may preclude the ability to slide a compression device up to a location proximal to the injury. Once the device, in its open state, has been located proximal to the injury, the buckle assembly [2] can be closed and the steps above to cinch and tighten the device can be performed.

The mating of the adjustable side [2a] and the non-adjustable side [2b] of the buckle assembly [2] at separation point [7] (as shown in FIG. 2) can be achieved through a number of designs. Buckle assembly [2] can hold firm under significant tension, such that it does not open accidentally. Designs for mating the two halves of the buckle assembly [2] include but are not limited to: snap-fit buckle designs, hook-and-loop buckles, surcingle buckles and stabbing buckle designs, for example, as described in U.S. Pat. No. 8,561,268, the entire teachings of which are incorporated herein by reference. Alternatively, the adjustable side [2a] and the non-adjustable side [2b] of the buckle assembly [2] can be inseparable. Buckle assembly [2] can be formed from a sliding buckle in which the adjustable side [2a] includes a sliding, adjustable bar. In a further alternative embodiment, the adjustable side [2a] of the buckle assembly [2] includes a stationary bar around which cinch strap [5] is routed and which permits a locking action to be accomplished by friction between the inner portion [5a] and outer portion [5b] after tension is applied.

The tightening mechanism [1] shown in FIG. 1 can take the form of a ratcheting buckle (as pictured) or an alternate tightening mechanism that can provide a mechanical advantage to a user, such as a windlass assembly, as described in International Application Number PCT/US15/14306. The tightening mechanism [1] can be connected to the cinch strap [5] using webbing or strap material that is connected to the guidance slide [3] and buckle assembly [2] through, for example, anchor points [22, 24]. The tightening mechanism [1] generates a mechanical advantage, shortening the distance between guidance slide [3] and the non-adjustable side [2b] of the buckle assembly [2]. This contractile action can result in an increase in circumferential pressure, in addition to the circumferential pressure obtained during cinching of the device with jamming feature/pull tab [5c]. The additional circumferential pressure applied by tightening mechanism [1] can be sufficient to occlude all or most blood flow from a severely-damaged limb when the device is used as a tourniquet.

Figure 3:
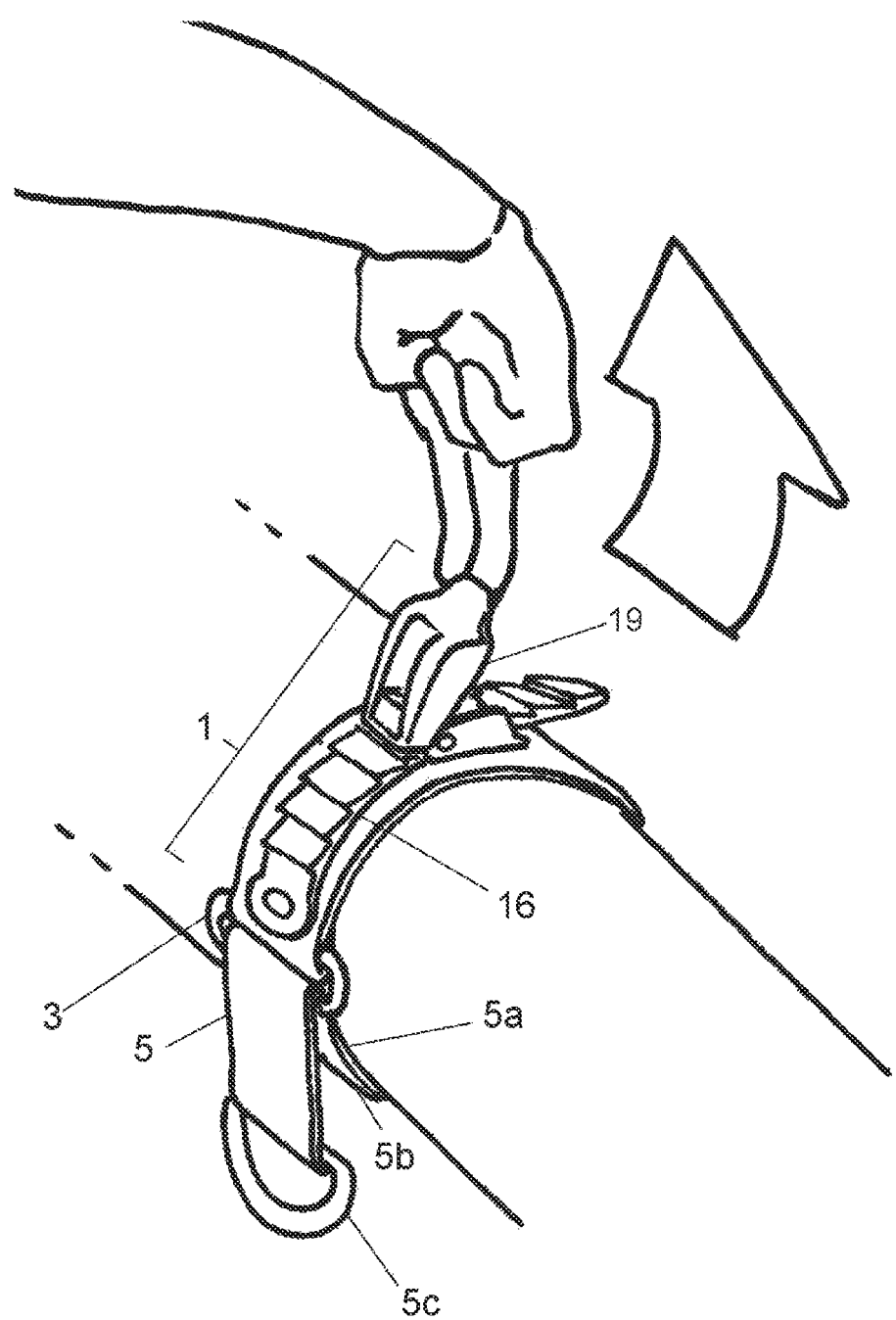
FIG. 3 illustrates the application of a compression device on a limb.

The tightening mechanism [1] assembly can allow for the starting distance between guidance slide [3] and non-adjustable side [2b] on the buckle assembly [2] to decrease. As illustrated in FIGS. 1 and 3, tightening mechanism [1] can be attached to a webbing or strap material that has sufficient flexibility to fold up as the contractile action of the tightening mechanism [1] causes the distance between guidance slide [3] and the non-adjustable side [2b] of the buckle assembly [2] to shorten. For example, the ratcheting buckle tightening mechanism pictured in FIG. 1 includes a ratchet lever [19] and a ratchet ladder strap [16] fastened to the base webbing or strap material at opposite ends of the tightening mechanism [1]. To operate the ratcheting buckle tightening mechanism, the ratchet lever [19] is lifted repeatedly which draws the ratchet ladder strap [16] towards the ratchet lever [19] as shown in FIG. 3. Due to a mechanical advantage, the actuation of this tightening mechanism [1] can produce significant tension. Mechanical cams that are internal to the ratchet lever [19] can engage the ratchet ladder strap [16] to maintain the tension originally developed by repeatedly lifting the ratchet lever [19] after the ratchet lever [19] had been released. A suitable ratcheting mechanism is described in U.S. Pat. No. 8,652,164, the entire teachings of which are incorporated herein by reference. For a windlass type tightening mechanism, such as that described in International Application Number PCT/US15/14306, an additional tightening webbing or strap can be fed through a windlass stick, forming a helix when the windlass stick is twisted pulling together the guidance slide [3] and the non-adjustable side [2b] of the buckle assembly [2]. Alternate tightening mechanism [1] designs include but are not limited to windlass, pulley and ratchet designs, both of which can effect a mechanical advantage for increasing circumferential pressure applied by the compression device after the rapid cinch step (sharp pull on the jamming feature/pull-tab [5c]) has been completed.

Alternatively, a connecting member, with or without a tightening mechanism, can be used to couple the guidance slide [3] and the non-adjustable side [2b] of the buckle assembly [2]. Guidance slide [3] could alternatively be directly coupled to the non-adjustable side [2b] of the buckle assembly [2]. Buckle assembly [2] is shown in FIG. 1 as being placed a short distance away from guidance slide [3]; however, buckle assembly [2] may be located at varying distances from guidance slide [3]. Placing the buckle assembly [2] farther from guidance slide [3] shortens the portion of the circumference of the device formed from cinch strap [5]. Having a larger portion of the circumference of the untightened device formed from cinch strap [5] (by, for example, placing buckle assembly [2] closer to guidance slide [3]) provides a greater range for untightened to tightened circumferences of the device.

The guidance slide [3], which is used to connect one side of the tightening mechanism [1] to the cinch strap [5], is a rigid loop. The guidance slide [3] is to be correctly sized for the width of webbing or strap material used, whilst ensuring that the anchor points securing the tightening mechanism [1] and the cinch strap [5] to the guidance slide [3] do not interfere with the inner portion of the cinch strap [5a] moving through the center of guidance slide [3], when the jamming feature/pull-tab [5c] is pulled to cinch.

An additional feature that is not shown in the figures but has been identified to be beneficial is a mechanism by which the jamming feature/pull-tab [5c] is held against the outer portion of the cinch strap [5b] so that the pull-tab is not inadvertently actuated prematurely. Such a mechanism could be a hook and loop fastener (such as Velcro), a clip, clasp, or button, or similar device.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compression device, comprising:
    a guidance slide;
    a jamming feature;
    a buckle assembly with both an adjustable, locking and non-adjustable side; and
    a cinch strap with both an inner and outer portion, the portions being inner and outer with respect to a center of the compression device, the inner portion anchored to the jamming feature, the outer portion anchored to the guidance slide,
        the cinch strap passing through the adjustable, locking side of the buckle assembly in such a way that pulling on the outer portion locks the adjustable, locking side and pulling on the inner portion allows the cinch strap to move freely through the adjustable, locking side,
        the inner portion of the cinch strap passing through the guidance slide to the adjustable, locking side of the buckle assembly,
        the outer portion of the cinch strap passing from the adjustable, locking side of the buckle assembly to the guidance slide,
        the non-adjustable side of the buckle assembly coupled to the guidance slide,
        the buckle assembly releasably mating the adjustable, locking side and the non-adjustable side,
        the coupled buckle assembly and cinch strap inner portion forming a loop for placing about an object, the inner circumference of the cinch strap being adjustable by pulling the jamming feature connected to the inner portion of the cinch strap, and the outer circumference of the cinch strap configured to maintain a minimum circumferential length after tension on the jamming feature is applied.

2. The compression device of claim 1, further comprising a tightening mechanism connecting the non-adjustable side of the buckle assembly to the guidance slide.

3. The compression device of claim 2, wherein the tightening mechanism is a self-holding ratcheting buckle system.

4. The compression device of claim 1, wherein the jamming feature is a pull-tab.

5. The compression device of claim 4, wherein the pull tab is a D-ring.

6. The compression device of claim 1, wherein the adjustable, locking side and non-adjustable side of the buckle assembly are separable from each other.

7. The compression device of claim 6, wherein the buckle assembly includes a male stabbing buckle with an adjustable, locking side and a female buckle with a non-adjustable side.

8. The compression device of claim 1, wherein the adjustable, locking side of the buckle assembly includes an adjustable bar.

9. The compression device of claim 1, wherein the adjustable, locking side of the buckle assembly includes a stationary bar and enables a locking action by friction between the inner and outer cinch straps.

10. The compression device of claim 1, wherein the cinch strap is webbing.

11. A method of compressing an object, comprising:
    providing the compression device of claim 1;
    placing the loop of the device about the object; and
    tightening the loop around the object by pulling the inner portion of the cinch strap.

12. A compression device, comprising:
    a guidance slide;
    a single-direction locking mechanism; and
    a cinch strap with both an inner and outer portion, the portions being inner and outer with respect to a center of the compression device,
        the outer portion anchored to the guidance slide,
        the cinch strap passing through the single-direction locking mechanism in such a way that pulling on the outer portion causes the locking mechanism to lock the cinch strap and pulling on the inner portion allows the cinch strap to move freely through the locking mechanism,
        the inner portion of the cinch strap passing from the locking mechanism through the guidance slide, the locking mechanism coupled to the guidance slide, the coupled locking mechanism and guidance slide and inner portion of the cinch strap forming a loop for placing about an object, the inner circumference of the cinch strap being adjustable by pulling the inner portion of the cinch strap, and the outer circumference of the cinch strap configured to maintain a minimum circumferential length after tension on the inner portion is applied.

* * * * *